US00PP08958P

United States Patent [19]

Heims

[11] Patent Number: Plant 8,958

[45] Date of Patent: Oct. 25, 1994

[54] PULMONARIA EXCALIBUR

[75] Inventor: Dan M. Heims, Portland, Oreg.

[73] Assignee: Terra-Nova Nurseries, Inc., Portland, Oreg.

[21] Appl. No.: 176,135

[22] Filed: Dec. 30, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Klarquist Sparkman Campbell Leigh & Whinston

[57] ABSTRACT

A new and distinct variety of Pulmonaria having unique metallic finish and coloration on foliage with undulating margins.

1 Drawing Sheet

The present invention relates to a new and distinct hybrid of Pulmonaria which originated as a cross-pollination of *Pulmonaria villarsae* 'Margery Fish' and *Pulmonaria saccharate* 'Argentea' in the Boraginaceae family.

The new Pulmonaria is a result of a controlled cross of the aforementioned plants at Terra-Nova Nursery in Portland, Oreg. This hybrid was selected from a large selection of seedlings. Mother plants were retained to observe habit and to compare with their progeny. The new variety has been reproduced only by asexual propagation (division and tissue culture). Each of the progeny exhibits identical characteristics to the original plant and is unlike any Pulmonaria offered by any American nursery or book as evidenced by the following characteristics:

(1) Spring, summer, and fail metallic silver leaves edged in dark green and slightly ruffled.

(2) Spring flowers in February through March of a wine-red to a pink hue.

Asexual propagation by division and tissue cultures done in Mt. Vernon, Wash., shows that the foregoing characteristics and distinctions come true to form and are established and transmitted through succeeding propagations.

BRIEF DESCRIPTION OF THE PHOTOGRAPHS:

DETAILED PLANT DESCRIPTION

Figure 1:
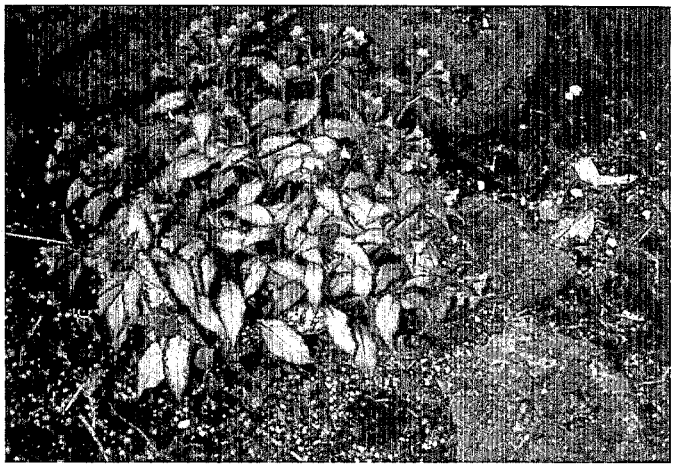
FIG. 1 is a spring picture showing the emerging leaves and flowers.
Figure 2:
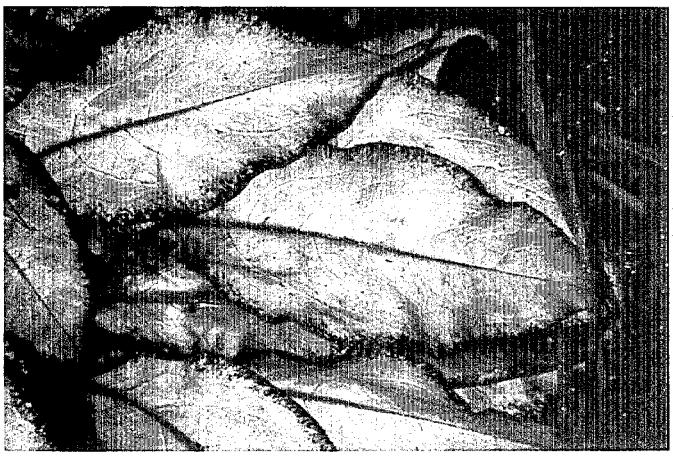
FIG. 2 is a picture showing the metallic silver foliage edged in dark green.

The following is a detailed description of the new Pulmonaria hybrid based on observations of specimens in Portalnd, Oreg. The color descriptions are all based on The Royal Horticultural Society Colour Chart.

Foliage:

*Type.*—Herbaceous
*Shape.*—Lanceolate
*Length.*—to 26 cm (10½ in).
*Width.*—10 cm (4 in).
*Petiole length.*—14 cm (5½ in)
*Margins.*—Undulate, entire

*Apex.*—Acute
*Base.*—Angustate
*Texture.*—Reticulate, Rough
*Leaf arrangement.*—Basal leaves, long-petioled
*Venation.*—Reticulate-pinnate Flower:

*Corolla.*—5 petalled
*Calyx.*—5 lobed
*Flower type.*—Complete, calyx tube urn-shaped, stamens exserted.
*Flower size.*—1 to 1.25 cm (0.4 to 0.5 in).
*Blooming habit.*—Bracted, terminal forked cymes
*Bloom period.*—February to March Color Characteristics Foliage:

*Mature leaves upper surface.*—Spring through fall: Greyed-Green Group 193C as metallic, bordered by Green Group 136B.
*Lower surfaced.*—Green Group 193A.

Flowers:

Violet-Blue Group 92A fading to Purple Group 75A.

DESCRIPTION OF PARENT PLANTS

This Pulmonaria hybrid has characteristics which makes it uniqe from its parents: *Pulmonaria villarsae* 'Margery Fish' and *Pulmonaria saccharatea* 'Argentea' (argentifolai). Pulmonaria villarsae 'Margery Fish' is described in the 'Pulmonaria' by Anthony Husley, June 1987, Horticulture Magazine, as having large marbled silver and green leaves. *Pulmonaria saccharata* 'Argentea' is described in the 'Pulmonaria' by Anthony Husley, June 1987, Horticulture Magazine, as having silver leaves with a light green edge and being smaller than Pulmonaria 'Excalibur'. *Pulmonaria saccharata* 'Argentea' has no undulation and differs in flower color'. No other Pulmonaria in commerce resembles Pulmonaria 'Excalibur'.

I claim:

1. A new and distinct hybrid of Pulmonaria substantially as shown and described, characterized by unique metallic finish and coloration on foliage with undulating margins.

* * * * *